(12) United States Patent
Bourillot et al.

(10) Patent No.: US 10,598,692 B2
(45) Date of Patent: Mar. 24, 2020

(54) DEVICE FOR THE VOLUMETRIC ANALYSIS OF AN ORGANIC OR INORGANIC SAMPLE

(71) Applicant: UNIVERSITE DE BOURGOGNE, Dijon (FR)

(72) Inventors: Eric Bourillot, Dijon (FR); Eric Lesniewska, Dijon (FR); Pauline Vitry, Moneteau (FR)

(73) Assignee: UNIVERSITE DE BOURGOGNE, Dijon (FR)

( * ) Notice: Subject to any disclaimer, the term of this patent is extended or adjusted under 35 U.S.C. 154(b) by 0 days.

(21) Appl. No.: 16/312,097

(22) PCT Filed: Jul. 25, 2017

(86) PCT No.: PCT/FR2017/052058
§ 371 (c)(1),
(2) Date: Dec. 20, 2018

(87) PCT Pub. No.: WO2018/020133
PCT Pub. Date: Feb. 1, 2018

(65) Prior Publication Data
US 2019/0227098 A1 Jul. 25, 2019

(30) Foreign Application Priority Data
Jul. 26, 2016 (FR) .................... 16 57168

(51) Int. Cl.
*G01Q 60/32* (2010.01)
*G01N 29/06* (2006.01)
(Continued)

(52) U.S. Cl.
CPC ......... *G01Q 60/32* (2013.01); *G01N 29/0663* (2013.01); *G01N 29/0681* (2013.01);
(Continued)

(58) Field of Classification Search
CPC .......... G01N 29/0663; G01N 29/0681; G01N 29/2418; G01N 29/2437; G01Q 60/32; G01Q 60/363
See application file for complete search history.

(56) References Cited

U.S. PATENT DOCUMENTS

| 8,448,261 B2 * | 5/2013 | Passian | G01Q 60/32 850/37 |
| 2006/0037401 A1 * | 2/2006 | Shekhawat | G01N 29/0663 73/603 |

(Continued)

FOREIGN PATENT DOCUMENTS

| JP | H08-21826 A | 1/1996 |
| JP | 2006153574 A | 6/2006 |

OTHER PUBLICATIONS

Ewald, M., et al. "From surface to intracellular non-invasive nanoscale study of living cells impairments." Nanotechnology 25.29 (2014): 295101. (Year: 2014).*

(Continued)

*Primary Examiner* — Wyatt A Stoffa
(74) *Attorney, Agent, or Firm* — Marshall, Gerstein & Borun LLP (57) ABSTRACT

An acoustic analysis device based on atomic force microscopy for the volume analysis of an organic or inorganic sample includes a support on which the sample is immobilized, and an atomic force microscopy lever having a free end provided with a part that interacts with an upper face of the sample and scans said upper face, one or at least two of the independent piezoelectric actuators supplying ultrasonic waves with interferential coupling, and acoustic measurement and analysis bodies associated with the atomic force microscopy lever. The support is a total reflection prism to which the piezoelectric actuators are applied, and the piezo- (Continued)

electric actuators are applied in determined positions on said prism in order to define determined angles of excitation of the ultrasonic waves.

14 Claims, 4 Drawing Sheets

(51) Int. Cl.
   *G01N 29/24* (2006.01)
   *G01Q 60/36* (2010.01)
(52) U.S. Cl.
   CPC ....... *G01N 29/2418* (2013.01); *G01Q 60/363* (2013.01); *G01N 2291/0427* (2013.01)

(56) References Cited

U.S. PATENT DOCUMENTS

| | | | | |
|---|---|---|---|---|
| 2008/0276695 | A1* | 11/2008 | Prater | G01Q 60/32 73/105 |
| 2009/0114024 | A1* | 5/2009 | Shekhawat | G01N 29/0663 73/603 |
| 2011/0036170 | A1* | 2/2011 | Shekhawat | G01N 29/0663 73/603 |
| 2011/0231966 | A1* | 9/2011 | Passian | B82Y 35/00 850/21 |
| 2014/0020141 | A1* | 1/2014 | Passian | G01Q 60/32 850/33 |

OTHER PUBLICATIONS

Vitry, Pauline, et al. "Combining infrared and mode synthesizing atomic force microscopy: Application to the study of lipid vesicles inside *Streptomyces* bacteria." Nano Research 9.6 (2016): 1674-1681. (Year: 2016).*
International Search Report issued in PCT Patent Application No. PCT/FR2017/052058 dated Nov. 7, 2017.
Written Opinion issued in PCT Patent Application No. PCT/FR2017/052058 dated Nov. 7, 2017.
Pauline et al., "Combining infraredand mode synthesizing atomic force microscopy: Application to the study of lipid vescibles inside *Streptomyces* bacteria," *Nano Research, Tsinghua University Press*, vol. 9, No. 6 (Apr. 2016).

* cited by examiner

DEVICE FOR THE VOLUMETRIC ANALYSIS OF AN ORGANIC OR INORGANIC SAMPLE

TECHNICAL FIELD

The present disclosure relates to the general technical field of atomic force microscopy (also called AFM or Atomic Force Microscopy). Atomic force microscopy is known under different variants, which will not be further detailed herein.

More particularly, the present disclosure concerns an acoustic analysis device the design and operation of which are based on atomic force microscopy for the volume analysis of organic or inorganic samples.

The basic technology of this disclosure is particularly promising for organic samples and especially for applications related to biology—healthcare on a cellular level, in their physiological environment.

Currently, intracellular tracking uses fluorescence microscopy detection or confocal microscopy to localize different organisms incorporated in a cell or a bacterium. However, these techniques have limited resolution due to diffusion.

Therefore, the present disclosure finds particular application in all fields where the nondestructive analysis and/or detection of early defects in material are necessary.

BACKGROUND

For example, an atomic force microscopy device (also called MS-AFM or Mode Synthesizing Atomic Force Microscopy) is known from U.S. Pat. No. 8,448,261 that in particular describes the use of two ultrasound waves applied near a measurement probe on the one hand, and a sample on the other. However, this known technology is not without major disadvantages. Indeed, the sources of ultrasound excitation near the lever (or probe) and the sample must be installed manually for each operator using this device, which can lead to a high degree of variability of positioning of the ultrasound excitation sources near the lever, and consequently a significant variation in the measured results.

Adding a piezoelectric actuator near the measurement lever results in a path of the light beam emitted by the laser diode which, after reflection on the end of said lever, is longer and offset relative to the initial path. Indeed, the lever supports as well as the levers are designed so that after reflection, the laser beam generally arrives on the mirror in order to be sent to a photodiode (photodetector). Even if there is an angular adjustment at the mirror in order to adjust the position of the laser spot on the photodiode; this adjustment is limited. The fact of having a piezoelectric actuator near the measurement lever, which is then positioned on its support, therefore generates an offset towards the bottom of the mirror of the optical path of the reflected laser beam. It is generally possible only to partially make up for this offset by returning the spot back onto the photodiode with a limited inclination of the mirror. However, often only a portion of the power of the laser spot is returned to the photodiode. This generates a signal loss affecting the reliability of measurements, and the adjustment of the device is not optimal. Due to the extent of observed offset, it is often difficult and even impossible to correctly center this laser spot.

Moreover, during measurements in a liquid medium, this phenomenon is accentuated by the phenomenon of refraction of the light rays. This technology is therefore unusable in liquid media.

Furthermore, these devices, which often use an ultrasound or piezoelectric excitation source placed beneath the sample, prevent an additional spectrum analysis from being performed.

Also known, for example from document US 2011/0231966, is an atomic force microscopy device (also called MS-AFM) that uses two ultrasound waves, one applied near a measurement probe and the other near a sample. However, the above-mentioned disadvantages also apply to such a configuration. In the aforementioned configuration, it is essential that the sample be disposed on a support (for example on a glass or metal slide) in order to adhere the piezoelectric actuator beneath the surface of the sample. This makes it possible to ensure a satisfactory transmission of the ultrasound waves. This operation requires the use of a heated adhesive. This can induce heating of the sample. Such heating can prove harmful for biological samples.

The use of such an adhesive, for example even for cold adhering, risks altering the sample due to the presence of harmful compounds such as solvents.

Moreover, in a particularly disadvantageous manner, the piezoelectric actuators of this device are not decoupled from the measurement lever.

Also known is the acoustic measurement device based on atomic force microscopy described in document JP H08 21826 A.

Conventionally this device comprises a cantilever the end of which includes a measurement point intended to interact with the surface of the sample and the vertical oscillations of which are analyzed by means of a laser device or a piezoelectric element situated on the point of the lever.

In this known device, the sample is placed on the upper face of a conventional parallelepiped-shaped support.

During analysis, Rayleigh type surface waves are generated at the surface of the sample by means of two transducers that are each mounted on an acrylic resin support, placed on the surface of the sample.

To be able to generate such surface waves, it is therefore essential that the transducers of this device be placed on the surface of the sample. Consequently, they cannot be moved against the support of the sample, and even less so against a face of this support spaced apart from the sample.

SUMMARY OF THE DISCLOSURE

As a result, the object of the present disclosure is to remedy the disadvantages of the prior art by providing a new acoustic analysis device enabling the performance of a non-destructive volume analysis of an organic or inorganic sample and to do so at a nanometric scale.

Another object of the present disclosure is to propose a new acoustic analysis device for the volumetric characterization of a sample, with performance that is improved relative to the known devices.

Another object of the present disclosure is to propose a new acoustic analysis device for volumetric characterization of a sample, the usage and adjustment of which are particularly simple and reliable.

Another object of the present disclosure is to propose a new, particularly advantageous acoustic analysis device, wherein the piezoelectric actuators are decoupled from the measurement lever.

The objects assigned to the disclosure are achieved by means of an acoustic analysis device based on atomic force microscopy for the volume analysis of an organic or inorganic sample, comprising:

a support on which the sample is immobilized, an atomic force microscopy measurement lever having a free end provided with a point intended to interact with an upper face of the sample and scan said upper face, at least two independent piezoelectric actuators mounted on mechanical supports and furnishing ultrasound waves generating multimodal interference coupling, acoustic measurement and analysis members associated with the measurement lever, to deliver results related to the volume characterization of the sample, comprising a laser diode that emits a light ray towards the lever and a photodetector that receives said light ray after reflection on the lever, characterized in that:

the support comprises a total-reflection prism, comprising one face on which the sample is disposed and at least one opposite face different from the face on which the sample is disposed against which the piezoelectric actuators are applied and does so at specific positions on said prism to define set angles of excitation of the ultrasound waves.

By definition, a total-reflection prism in the present disclosure is a 60° or 45° straight prism, or a semi-spherical or semi-cylindrical prism.

The angle of excitation is defined as being the angle between the faces of the prism on which the piezoelectric actuators are affixed and the face of the prism on which the sample is affixed.

According to a preferred embodiment of the device, the piezoelectric actuators are positioned symmetrically.

According to one embodiment of the device, the face on which the sample is disposed is a flat, preferably horizontal, face of the total-reflection prism.

According to one embodiment of the device, the face on which the sample is disposed is the upper face of the total-reflection prism.

According to one exemplary embodiment of the device, the total-reflection prism is a straight prism comprising a flat face on which the sample is disposed and two opposite faces.

The piezoelectric actuators are for example mounted on fixed mechanical supports and are each applied and immobilized against one of the two opposite faces of the straight prism by means of a layer of gel or adhesive.

According to another exemplary embodiment of the device, the total-reflection prism is a semi-cylindrical prism comprising a flat face on which the sample is disposed and a cylindrical face against which the piezoelectric actuators are applied.

The mechanical supports are for example mobile mechanical supports, for example motorized, enabling the piezoelectric actuators to move on the cylindrical face and thus to modify the angles of excitation of the ultrasound waves.

According to another exemplary embodiment of the device, the total-reflection prism is a semi-spherical prism comprising a flat face on which the sample is disposed and a spherical face against which the piezoelectric actuators are applied.

The mechanical supports are for example mobile mechanical supports, for example motorized, enabling the piezoelectric actuators to move on the spherical surface and thus to modify the angles of excitation and for the directions of propagation of the ultrasound waves. The direction of propagation corresponds to a vector defined by the generatrix perpendicular to the face of the prism on which the piezoelectric actuator is adhered.

According to another exemplary embodiment, the device comprises an additional light source and associated optical members in order to direct a light beam onto the upper face of the sample thus generating a thermal excitation.

According to another exemplary embodiment, the device comprises another light source and associated optical members in order to direct a light beam through the prism onto the lower face of the sample and then a total internal reflection in the sample, in order to direct said reflected light beam towards a spectrum analyzer preceded by an optical filter.

According to another exemplary embodiment of the device, the piezoelectric actuators and the fixed mechanical supports have respective aligned through-openings, which are disposed on the prism in such a way as to define the optical path of the incident and reflected light beam.

According to another exemplary embodiment, the device comprises four piezoelectric actuators. Such a configuration makes it possible, for example, to determine the directional impact of the ultrasound waves according to the geometry of the objects studied (cubic geometry, linear spherical geometry, etc.). This configuration also makes it possible to determine, in the case of crystalline samples, if there are axes of symmetry which could be revealed along the direction of propagation of the ultrasound waves. This configuration also makes it possible to determine if a simultaneous excitation of the four piezoelectric actuators, thus generating a so-called spherical wave, would reveal other details of the sample, compared to excitation of the sample by planar waves.

According to another example of the device, the constituent material of the prism is a solid organic material. In the case where the device is designed for adding optical excitation, depending on the nature of the wavelengths used, the nature of the constituent material of the prism is important. For example, in the case of infrared IR radiation, a material that does not absorb infrared radiation IR must be used for the prism. Since glass is a material that absorbs infrared IR radiation, it is then preferable to use ZnSe material.

According to another example, it is preferable to use a quartz material for ultraviolet UV radiation.

According to an exemplary embodiment, the measurement lever is an optical lever associated with an optical filter, which is followed by an additional spectrum analyzer.

One notable advantage of the device is that it makes it possible to perform a volume analysis with nanometric resolution without particular preparation of the sample, other than what is required by atomic force microscopy.

Another advantage of the device is the possibility of modifying the depth of investigation in a sample, thus allowing a volume analysis of the sample to be performed while preserving the resolution and the performance of the atomic force microscope.

Another advantage of the device is the fact that this new configuration makes it possible to work in a liquid medium, contrary to the known technology (MS-AFM or Mode-Synthesizing Atomic Force Microscopy).

Another advantage of the device is in its great simplicity of use.

Another advantage of the device is the possibility of performing nanometric volume analyses of a sample without using a marker.

Moreover, thanks to the device, the sample can be deposited directly onto the upper face of the prism, or the support of the sample can be affixed to the upper face of the prism by means of a gel. Such an operation does not produce any heating of the sample.

The performance of the device is improved thanks especially to better mechanical stability resulting from the fact that there is no piezoelectric actuator near the lever.

The device also makes it possible to improve the signal-to-noise ratio due to the fact that the laser beam can be centered correctly on a four-quadrant photodetector. Thus, as regards acoustic response, fewer "edge" effects of the waves are observed due to the symmetrical positioning of the piezoelectric actuators. For example, in figures produced on the same type of bacterium, the membrane wall induces member edge echoes providing a very marked contrast of the wall relative to the internal view of the elements of the bacterium. This contrast of the membrane wall is reduced with the device and enables better readability of the internal elements of the bacterium to be obtained.

BRIEF DESCRIPTION OF THE FIGURES

Other features and advantages of the disclosed embodiments will appear upon reading the detailed description which follows, which is made with reference to the accompanying drawings, wherein.

DETAILED DESCRIPTION

In the following, identical structural and functional elements shown in different figures bear the same numerical or alphanumerical references.

Moreover, identical structural and functional technical elements will not be described in detail for all embodiments of the device. The functioning of these elements is easily transposable from one exemplary embodiment to another.

Figure 1:
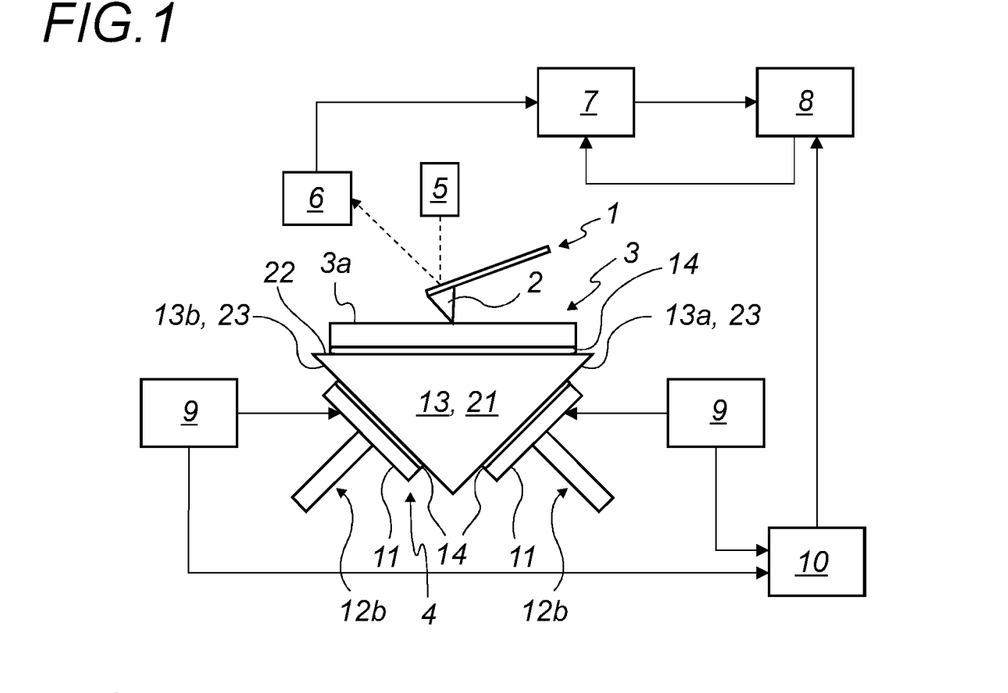
FIG. 1 is a schematic illustration of an exemplary embodiment of an acoustic analysis device.

FIG. 1 is a schematic illustration of a first exemplary embodiment of an acoustic analysis device.

The device comprises technical means pertaining to atomic force microscopy. Thus, the device comprises an atomic force microscopy measurement lever 1 (also called conventional AFM lever). Said lever 1 has a point 2 intended to interact with a sample 3 at the upper face 3a thereof.

The lever 1, and more specifically the point 2 of said lever 1, is therefore intended to approach and scan the upper face 3a. To that end, the device comprises mechanical actuators, not shown, to provide precisely a relative movement between the lever 1 and a support 4 on which the sample 3 is immobilized.

According to a preferred exemplary embodiment of the device, the lever 1 is mobile.

According to another exemplary embodiment, while in the AFM system it is the sample 3 that is moved, it may be considered that the assembly comprising the sample 3 and a prism, supporting said sample 3 and comprising piezoelectric actuators, is mobile.

The device further comprises acoustic measurement and analysis members associated with the measurement lever 1. Said measurement and analysis members preferably comprise, in a known manner, a laser diode 5 and a photodetector 6. The laser diode 5 thus emits a light ray onto the lever 1, which reflects said light ray towards the photodetector 6. Thus, a variation of position in space of the lever 1 could be detected on the photodetector 6 by a variation of position of the impact of the reflected light ray. The light ray is preferably a laser beam.

Preferably, the device also comprises a control unit 7, an amplifier 8, at least two function generators 9 and a frequency mixer 10. The function of these elements will be described hereinafter.

The device also comprises at least two ultrasound excitation sources consisting of piezoelectric actuators 11. Said actuators are each mounted on a mechanical support 12.

The support 4 of the device comprises a total-reflection prism 21 that includes a face 22 on which the sample 3 is disposed and one or two opposite faces 23 which are different from the face 22 on which the sample 3 is disposed, and against which the piezoelectric actuators 11 are applied.

The face 22 on which the sample 3 is disposed is a substantially flat, preferably horizontal, face of the total-reflection prism 21. It generally involves the upper face of the prism.

Depending on the nature thereof, the prism 21 also includes one or two opposite faces 23, namely two flat faces 13a and 13b in the case of a straight prism 13, a cylindrical face C in the case of a semi-cylindrical prism 15, or a spherical surface S in the case of a semi-spherical prism 16.

In the exemplary embodiment represented in FIG. 1, the support 4 includes a straight prism 13 having two opposite faces 13a and 13b each having a piezoelectric actuator 11. Each piezoelectric actuator 11 is advantageously adhered to one face 13a, 13b by means of a layer 14 of gel or glue. An additional layer 14, for example, serves to immobilize the sample 3 on the upper face 22 extending substantially horizontally.

Figure 2:
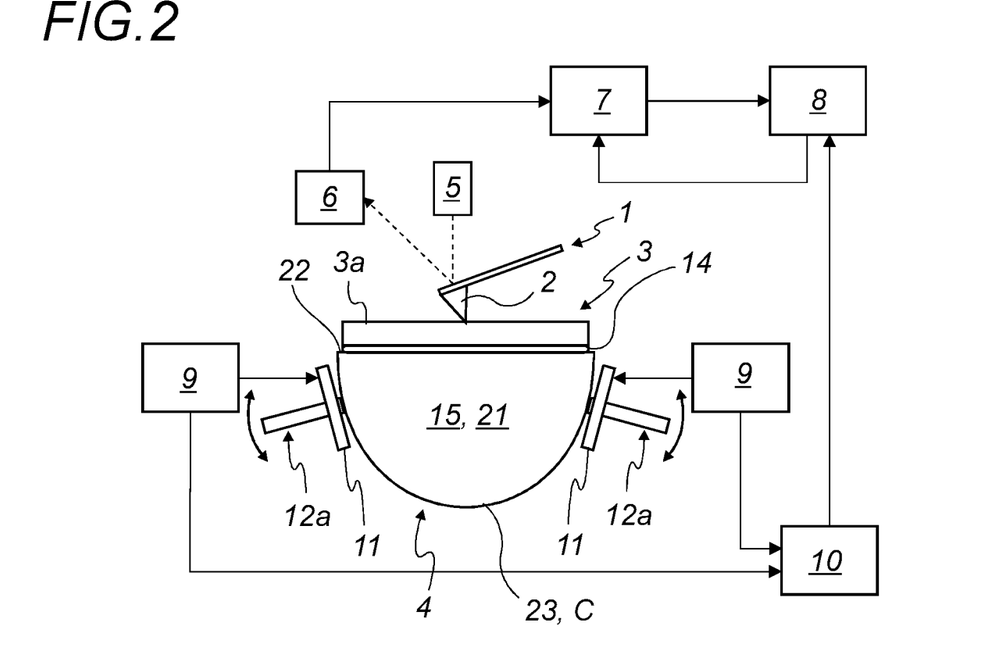
FIG. 2 is a schematic illustration of another exemplary embodiment of the acoustic analysis device.

In the exemplary embodiment of the device, represented in FIG. 2, the support 4 includes a semi-cylindrical prism 15. The sample 3 is immobilized on the flat upper face 22 of the semi-cylindrical prism 15.

The piezoelectric actuators 11 are mounted on mobile mechanical supports 12b, for example, motorized and disposed substantially facing each other and in contact with the cylindrical face C of the semi-cylindrical prism 15.

The movement of the mobile mechanical supports 12b on a cylindrical surface makes it possible to modify the angles of excitation of the ultrasound waves.

Figure 5:
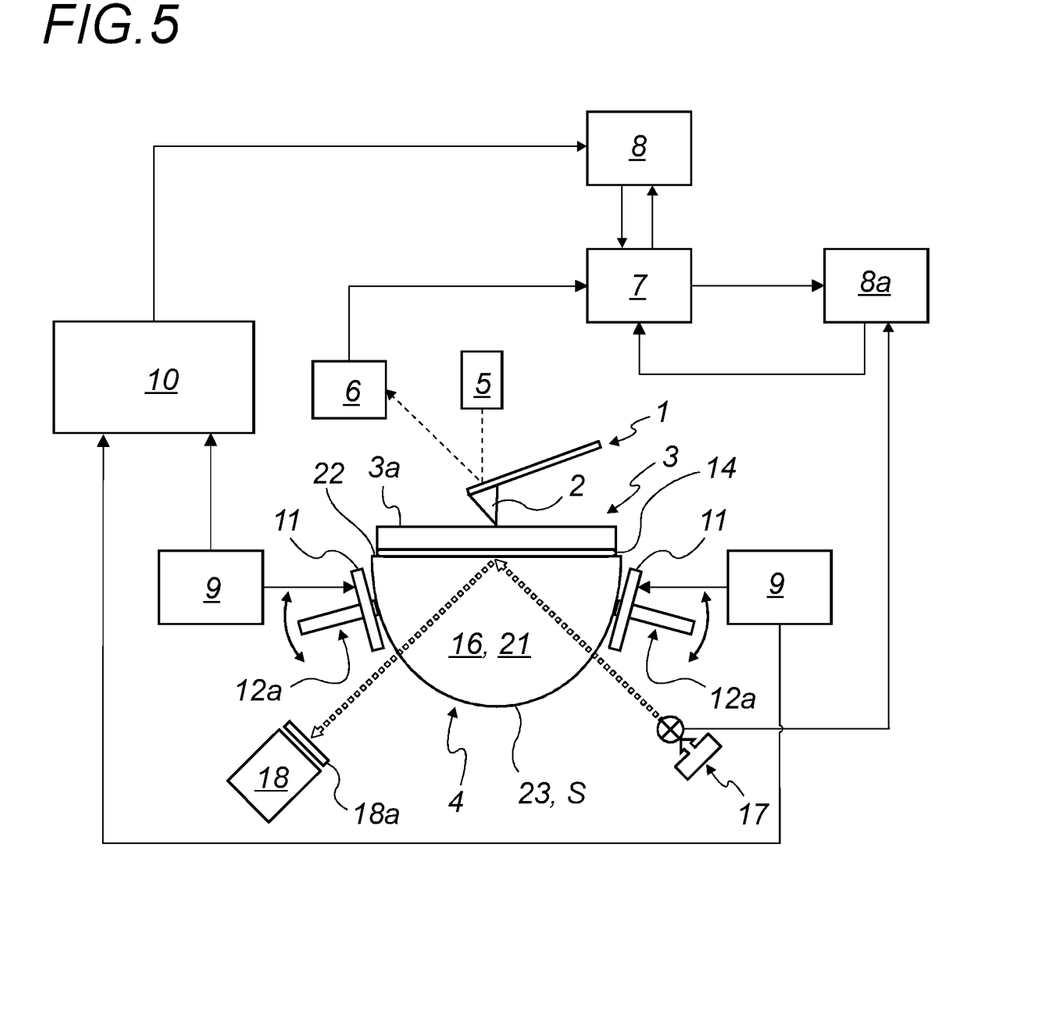
FIG. 5 is a schematic illustration of another embodiment of the acoustic analysis device of FIG. 2.

In the exemplary embodiment of the device, represented in FIG. 5, the support 4 includes a semi-spherical prism 16. The movement of the mobile mechanical supports 12b on a spherical surface S advantageously makes it possible to modify the angles of excitation and/or the directions of propagation of the ultrasound waves.

The device of FIG. 5 comprises a light source 17 and associated optical members, which are known, to direct a light beam through the prism 13, 15 or 16, onto the lower face of the sample 3. After a total internal reflection in the sample 3, the reflected beam is directed towards a spectrum analyzer 18 preceded by an optical filter 18a. The light source 17 is advantageously connected to a supplemental amplifier 8a of the device.

Figure 4:
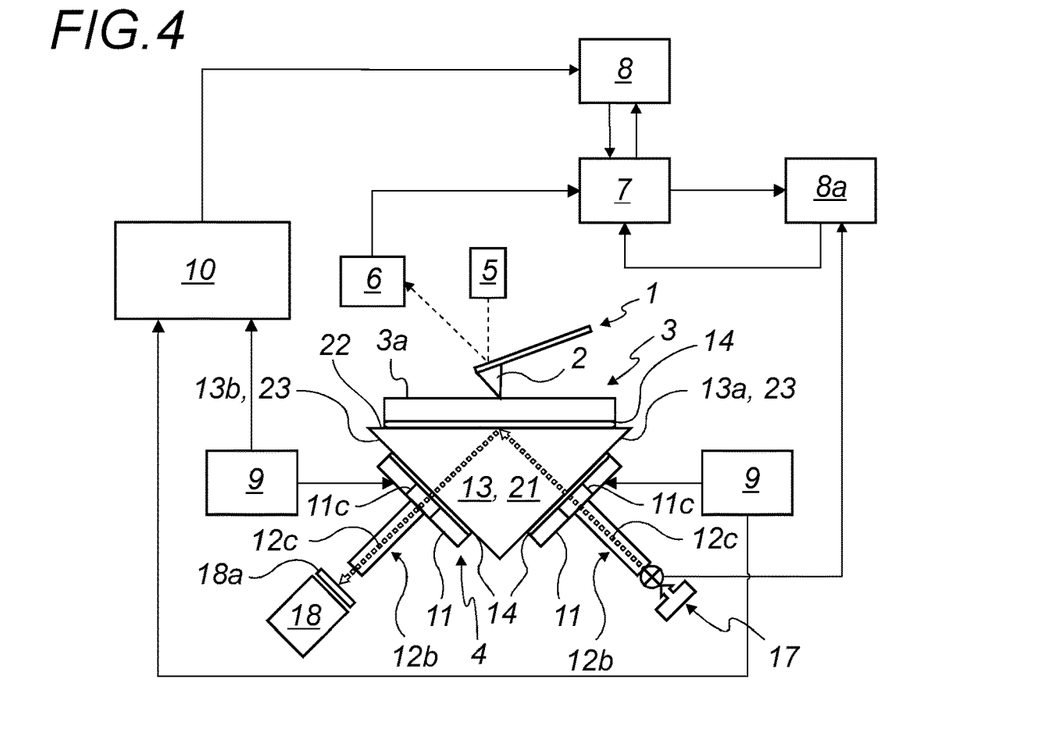
FIG. 4 is a schematic illustration of another exemplary embodiment of the acoustic analysis device.

In the exemplary embodiment of the device represented in FIG. 4, the piezoelectric actuator 11 and the associated fixed mechanical support 12b have respective through-openings 11c, 12c. Said openings are aligned so as to define the optical path of the incident and reflected light beams originating from the light source 17.

The light source 17 as well as the spectrum analyzer 18 are then advantageously mounted on the fixed mechanical supports 12b.

Figure 3:
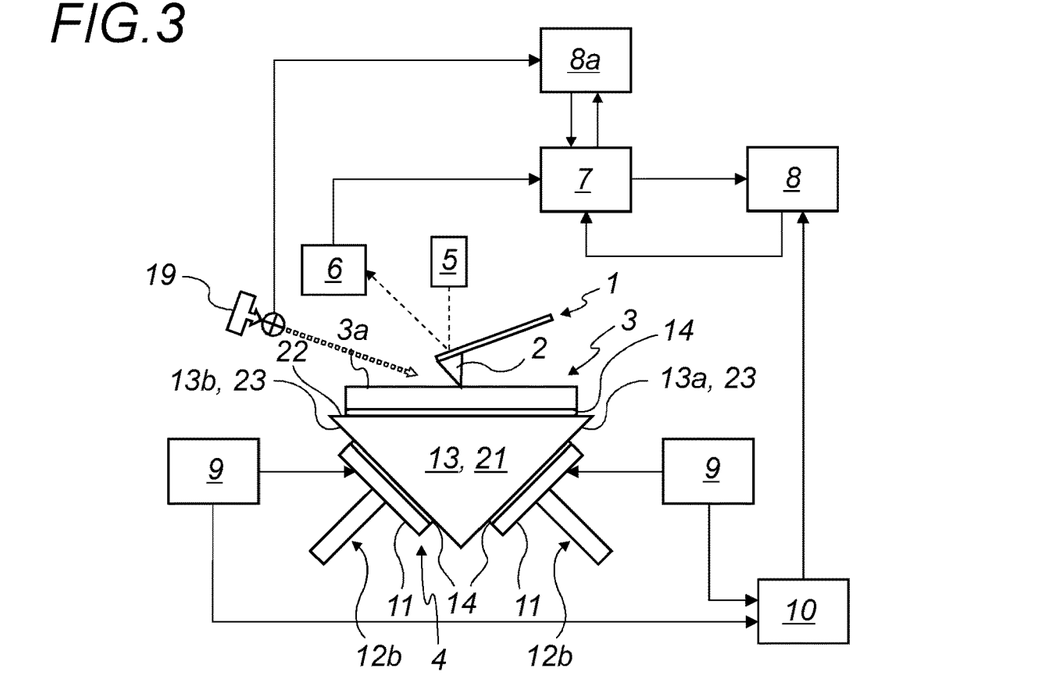
FIG. 3 is a schematic illustration of another embodiment of the acoustic analysis device of FIG. 1.

In the exemplary embodiment represented in FIG. 3, the acoustic analysis device comprises an additional infrared light source 19 and known associated optical members, in order to direct a light beam onto the upper face 3a of the sample 3. The light beam generates a thermal excitation in the sample 3. This thermal excitation will preferentially excite certain molecules depending on their specific absorption capacities (characteristics related to the nature of the chemical bonds of the molecules). This thermal excitation will then be sensed by the lever 1 due to different frequency vibrations of said lever 1, and recorded by the photodetector 6. These vibrations then correspond to specific absorption wavelengths in the infrared range when the light beam is infrared radiation. Thus, depending on the nature of the chemical species to be characterized, it is sufficient to select a single wavelength characteristic of a single type of chemical bond, in order to obtain a chemical species cartography as well as the volume analysis provided by the acoustic microscopy.

In the exemplary embodiment illustrated in FIG. 3, as well as in the exemplary embodiments illustrated in FIGS. 4 and 5, the light sources 19 and 17 are connected to the additional amplifier 8a, which itself is connected to the control unit 7.

The control unit 7 is the unit for controlling AFMs that manages the usual signals from an AFM. Generally, it also enables access to outside signals (input/output). In the case of the disclosed embodiments, it makes it possible to acquire the outside signals pertaining to the phase and amplitude signal of the acoustic signal detected by the measurement lever 1. These signals (amplitude and phase) from the acoustic wave are detected by the measurement lever 1 and come from the excitation of the PZT actuators placed on the sides of the prism 13, 15 or 16.

In order to extract this information detected by the measurement lever 1, synchronous detection is used by means of an amplifier 8, connected directly to the frequency mixer 10 into which the frequency of the desired acoustic wave is injected as reference signal.

Furthermore, the signal detected by the measurement lever 1 is recorded via the photodetector 6, thanks to the reflection of the laser beam on the lever 1 towards the photodetector 6, as with any AFM.

This signal is recorded "electronically" by the control unit 7 of the microscope. This information is accessible as an external signal from the control unit 7 and is therefore sent as an input signal to the amplifier 8 (synchronous detection). The detection then extracts the signal at the reference frequency from the input signal and gives it the amplitude and phase which are transmitted to the control unit 7 as external signals to be recorded. These signals fall within a range of electric voltages between +10 V and −10 V.

In the exemplary embodiments, illustrated in FIGS. 3, 4 and 5, the possibility is added that said device can be adapted on devices having an optical analysis system as well as the AFM. These optical analysis systems may require the use of a modulated optical signal (light sources 19 or 17 in the figures) in order to limit the heating of the sample 3 due to the light source. Since said optical signal is modulated, this signal must be detected at the modulation frequency via synchronous detection by means of an amplifier 8a.

Concerning the analysis of these optical signals, it can be done in reflection, either by performing a spectral analysis (with a spectrum analyzer), or by imaging the reflected signal by a photon detector or CCD camera, in order to measure the absorption for example.

Such optical devices can have various forms and use various sources or various detectors, depending on the optical devices developed by the microscope manufacturers or even developed by the users. Thus, the device can fulfill an infrared spectroscopy function developed on AFM.

In the embodiments of the device illustrated in FIGS. 4 and 5, the spectrum analyzer 18, associated with the optical filter 18a thereof, can be used to perform, in addition to atomic force microscopy, detection of fluorescence, detection of surface plasmons (SPR), or surface-enhanced Raman spectroscopy (SERS). The spectrum analyzer 18 is used for optical detection at the prism output by reflection. Advantageously, the incident light is used, at a given frequency, for better identification of the acquisition frequency of the optical signal.

The optical devices used generally serve to detect or identify chemical/biological species either by detection of markers (fluorescence) or identification by specific interactions (SPR, SERS), or by specific absorptions. These techniques are generally limited in spatial resolution (at best one hundred nanometers) and in volume analysis. Diffusion phenomena make it possible to detect the presence but does not allow localizing the species inside a body such as a cell. The device therefore allows a better localization of the species of interest.

Figure 6:
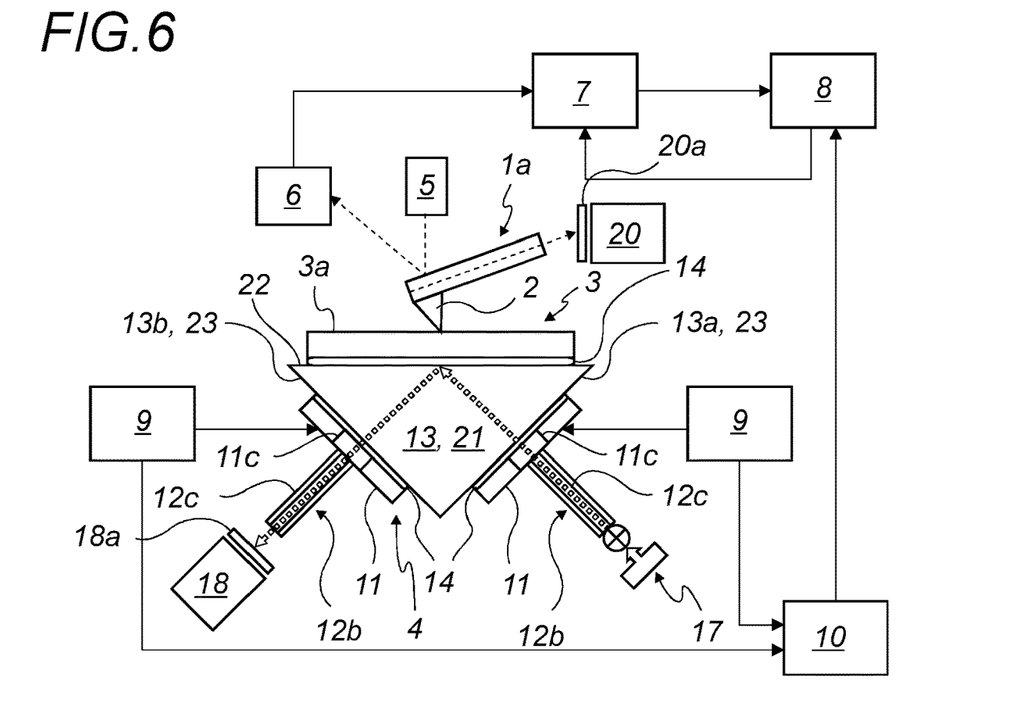
FIG. 6 is a schematic illustration of another exemplary embodiment of the acoustic analysis device comprising an optical measurement lever.

In the exemplary embodiment of the device represented in FIG. 6, the measurement lever 1 is replaced by an optical level 1a. Said optical level transmits optical signals from the sample 3 to an additional spectrum analyzer 20 preceded by an optical filter 20a.

Figure 7:
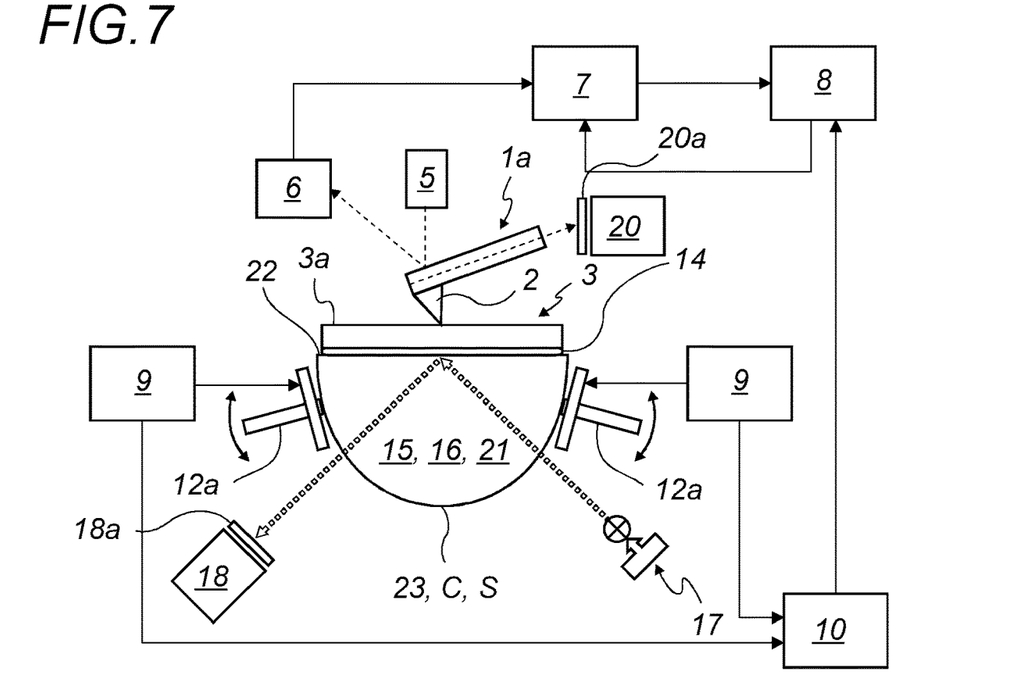
FIG. 7 is a schematic illustration of an additional exemplary embodiment of the acoustic analysis device, comprising an optical measurement lever.

The device illustrated in FIG. 7 differs from the devices of FIGS. 2 and 5 by the presence of the optical lever 1a, replacing the measurement lever 1. Said optical lever 1a is also associated with an additional spectrum analyzer 20 preceded by an optical filter 20a.

The benefit of using the optical lever 1a is that it makes it possible to simultaneously acquire, at each point of a single sample 3, the typography signal (like the conventional AFM lever), the acoustic signal in amplitude and phase, as well as the optical signal coming from said sample 3 as a result of the light source 17. The optical lever 1a thus allows the range of usable and detectable wavelengths to be extended. Thus, with such optical lever 1a, wavelengths can be detected ranging from near-infrared IR to visible, and where applicable, up to near ultraviolet UV, while the exemplary embodiment illustrated for example in FIG. 3 functions only in infrared IR.

The device is notable in that it makes it possible to obtain better precision than what is obtained in a known MS-AFM configuration.

Indeed, this is confirmed by the comparison of results obtained with calibrated samples of polymers, the structure of which has been locally modified by an electron beam. In particular, the device has made it possible to establish a volumetric change cartography of the density of samples, and it does so with precision and reliability.

Obviously, the contemplated embodiments are not limited to the preferred embodiments described above and shown in the various figures, a person skilled in the art being able to make numerous modifications and imagine other embodiments within the limits of the appended claims. Thus, a described technical characteristic can be replaced by an equivalent technical characteristic without leaving the framework or scope of the disclosure.

The invention claimed is:

1. An acoustic analysis device based on atomic force microscopy for volume analysis of an organic or inorganic sample comprising:
   a support on which the sample is immobilized,
   an atomic force microscopy measurement lever having a free end provided with a point intended to interact with an upper face of the sample and scan said upper face,
   at least two independent piezoelectric actuators mounted on mechanical supports and furnishing ultrasound waves generating multimodal interference coupling,
   acoustic measurement and analysis members associated with the measurement lever, to deliver results related to the volume analysis of the sample, comprising a laser diode that emits a light ray towards the lever and a photodetector that receives said light ray after reflection on the lever, wherein
   the support comprises a total-reflection prism, comprising one face on which the sample is disposed and at least one opposite face, different from the face on which the sample is disposed, against which the piezoelectric actuators are applied and does so at preset positions on said prism to define set angles of excitation of ultrasound waves.

2. The device according to claim 1, wherein the piezoelectric actuators are positioned symmetrically.

3. The device according to claim 1, wherein the face on which the sample is disposed is a flat face of the total-reflection prism.

4. The device according to claim 1, wherein the face on which the sample is disposed is an upper face of the total-reflection prism.

5. The device according to claim 1, wherein the total-reflection prism is a straight prism comprising a flat face on which the sample is disposed and two opposite faces; and wherein the piezoelectric actuators are mounted on fixed mechanical supports and are each applied and immobilized against one of the two opposite faces of the straight prism by means of a layer of gel or adhesive.

6. The device according to claim 1, wherein the total-reflection prism is a semi-cylindrical prism comprising a flat face on which the sample is disposed and a cylindrical face against which the piezoelectric actuators are applied, and wherein the mechanical supports are mobile supports enabling the piezoelectric actuators to move on the cylindrical face and thus to modify the angles of excitation of the ultrasound waves.

7. The device according to claim 1, wherein the total-reflection prism is a semi-spherical prism comprising a flat face on which the sample is disposed and a spherical face against which the piezoelectric actuators are applied, and wherein the mechanical supports are mobile supports enabling the piezoelectric actuators to move on the spherical surface and thus to modify the angles of excitation and/or directions of propagation of the ultrasound waves.

8. The device according to claim 1, further comprising a light source and associated optical members for directing an incident light beam through the prism onto a lower face of the sample and then, after a total internal reflection in the sample, for detecting a reflected light beam towards a spectrum analyzer preceded by an optical filter.

9. The device according to claim 8, wherein the total-reflection prism is a straight prism comprising a flat face on which the sample is disposed and two opposite faces, wherein the piezoelectric actuators are mounted on fixed mechanical supports and are each applied and immobilized against one of the two opposite faces of the straight prism by means of a layer of gel or adhesive, and wherein the piezoelectric actuators and the fixed mechanical supports have respective aligned through-openings, which are disposed on the straight prism in such a way as to define an optical path of the incident and reflected light beam.

10. The device according to claim 1, further comprising an additional light source and associated optical members in order to direct a light beam onto an upper face of the sample thus generating a thermal excitation.

11. The device according to claim 1, further comprising four piezoelectric actuators.

12. The device according to claim 1, wherein constituent material of the prism is a solid, organic material.

13. The device according to claim 1, wherein the measurement lever is an optical lever associated with an optical filter, followed by an additional spectrum analyzer.

14. The device according to claim 1, wherein the face on which the sample is disposed is a flat, horizontal face of the total-reflection prism.

* * * * *